US011376050B2

(12) United States Patent
DiVincenzo et al.

(10) Patent No.: US 11,376,050 B2
(45) Date of Patent: Jul. 5, 2022

(54) BONE SCREW (71) Applicant: Medos International Sarl, Le Locle (CH)

(72) Inventors: John DiVincenzo, Weymouth, MA (US); Nicholas Pavento, North Attleboro, MA (US); Ralph Solitario, Pocasset, MA (US); Eric Biester, Providence, RI (US)

(73) Assignee: Medos International Sarl, Le Locle (CH)

( * ) Notice: Subject to any disclaimer, the term of this patent is extended or adjusted under 35 U.S.C. 154(b) by 30 days.

(21) Appl. No.: 15/633,969

(22) Filed: Jun. 27, 2017

(65) Prior Publication Data
US 2018/0368898 A1 Dec. 27, 2018

(51) Int. Cl.
*A61B 17/86* (2006.01)
*A61B 17/70* (2006.01)
A61B 90/00 (2016.01)

(52) U.S. Cl.
CPC ...... *A61B 17/8635* (2013.01); *A61B 17/7032* (2013.01); *A61B 17/863* (2013.01); *A61B 17/7085* (2013.01); A61B 2090/037 (2016.02)

(58) Field of Classification Search
CPC ............ A61B 17/8635; A61B 17/8625; A61B 17/863; A61B 17/864
See application file for complete search history.

(56) References Cited

U.S. PATENT DOCUMENTS

| 5,300,076 | A | 4/1994 | Leriche |
| 5,364,400 | A | 11/1994 | Rego, Jr. et al. |
| 5,443,509 | A | 8/1995 | Boucher et al. |
| 5,593,410 | A | 1/1997 | Vrespa |
| 5,733,307 | A | 3/1998 | Dinsdale |
| 5,928,236 | A | 7/1999 | Augagneur et al. |
| 5,968,078 | A | 10/1999 | Grotz |
| 6,306,140 | B1 * | 10/2001 | Siddiqui .............. A61B 17/863 606/315 |
| 6,398,785 | B2 | 6/2002 | Carchidi et al. |
| 6,517,542 | B1 | 2/2003 | Papay et al. |
| 6,736,820 | B2 | 5/2004 | Biedermann et al. |

(Continued)

FOREIGN PATENT DOCUMENTS

FR  2932975 A1  1/2010
FR  2971138 A1  8/2012

(Continued)

OTHER PUBLICATIONS

Extended European Search Report issued in European Application No. 18824954.4, dated Feb. 24, 2021, 7 pages.

(Continued)

*Primary Examiner* — Amy R Sipp
(74) *Attorney, Agent, or Firm* — Mintz Levin Cohn Ferris Glovsky and Popeo, P.C.

(57) ABSTRACT

Various bone screws configured to be implanted into bone and methods of use are provided. In an exemplary embodiment, a bone screw is provided with an elongate shank and a head with a drive feature configured to couple with a driver tool for being advanced into bone and a threaded shank. The screw can have a distal end or tip that has one or more cutting edges thereon configured to cut bone as the bone screw is inserted into bone.

20 Claims, 7 Drawing Sheets

(56) References Cited

U.S. PATENT DOCUMENTS

| | | |
|---|---|---|
| 6,743,233 B1 | 6/2004 | Baldwin et al. |
| 6,755,835 B2 | 6/2004 | Schultheiss et al. |
| 6,974,460 B2 | 12/2005 | Carbone et al. |
| 7,008,227 B2 | 3/2006 | Carmichael et al. |
| 7,179,261 B2 | 2/2007 | Sicvol et al. |
| 7,198,488 B2 | 4/2007 | Lang et al. |
| 7,819,905 B2 | 10/2010 | Newcomb et al. |
| 8,029,285 B2 | 10/2011 | Holmen et al. |
| 8,267,977 B2 * | 9/2012 | Roth .................... A61B 17/562 606/301 |
| 8,333,590 B2 | 12/2012 | Hansson |
| 8,414,628 B2 | 4/2013 | Melkent |
| 8,945,190 B2 | 2/2015 | Culbert et al. |
| 9,079,263 B2 | 7/2015 | Reed |
| 9,168,077 B2 | 10/2015 | Whitmore |
| 9,358,057 B1 | 6/2016 | Whipple et al. |
| 9,848,962 B2 | 12/2017 | Moon et al. |
| 10,092,341 B2 | 10/2018 | Ellis |
| 10,772,667 B2 | 9/2020 | Ramsay et al. |
| 2003/0069582 A1* | 4/2003 | Culbert ................ A61B 17/742 606/65 |
| 2004/0044345 A1 | 3/2004 | DeMoss et al. |
| 2004/0106925 A1 | 6/2004 | Culbert |
| 2005/0021036 A1 | 1/2005 | Whitmore et al. |
| 2005/0101961 A1 | 5/2005 | Huebner et al. |
| 2006/0100627 A1 | 5/2006 | Stone et al. |
| 2006/0217727 A1 | 9/2006 | Munro et al. |
| 2007/0162028 A1* | 7/2007 | Jackson ............. A61B 17/8635 606/86 A |
| 2010/0069970 A1 | 3/2010 | Lewis et al. |
| 2010/0114174 A1 | 5/2010 | Jones et al. |
| 2010/0211118 A1 | 8/2010 | Christen et al. |
| 2011/0070558 A1 | 3/2011 | Park et al. |
| 2011/0288599 A1 | 11/2011 | Michielli et al. |
| 2011/0295319 A1 | 12/2011 | Duplessis et al. |
| 2012/0203290 A1* | 8/2012 | Warren ............. A61B 17/1671 606/86 A |
| 2012/0232599 A1 | 9/2012 | Schoenly et al. |
| 2013/0053901 A1 | 2/2013 | Cormier et al. |
| 2013/0096618 A1 | 4/2013 | Chandanson et al. |
| 2014/0058460 A1 | 2/2014 | Reed |
| 2014/0058461 A1 | 2/2014 | Black |
| 2014/0081339 A1 | 3/2014 | Bowman et al. |
| 2014/0114312 A1 | 4/2014 | Krause |
| 2014/0234800 A1 | 8/2014 | Laster |
| 2014/0257409 A1 | 9/2014 | Reed |
| 2014/0277188 A1 | 9/2014 | Poulos |
| 2014/0303676 A1 | 10/2014 | Stroncek et al. |
| 2015/0044639 A1 | 2/2015 | Carlsson et al. |
| 2015/0196388 A1 | 7/2015 | Housman et al. |
| 2016/0081771 A1 | 3/2016 | Fromovich et al. |
| 2016/0113693 A1 | 4/2016 | Denis et al. |
| 2016/0120583 A1* | 5/2016 | Bales ................ A61B 17/8625 606/304 |
| 2018/0303529 A1 | 10/2018 | Zastrozna |
| 2019/0223917 A1 | 7/2019 | Gray et al. |
| 2020/0367952 A1 | 11/2020 | Ramsay et al. |

FOREIGN PATENT DOCUMENTS

| | | |
|---|---|---|
| FR | 2971413 A1 | 8/2012 |
| FR | 3000662 A3 | 7/2014 |
| FR | 3000664 A3 | 7/2014 |
| FR | 3021206 A1 | 11/2015 |
| JP | 2013526374 A | 6/2013 |
| JP | 2014529446 A | 11/2014 |
| JP | 2020517341 A | 6/2020 |
| WO | 2015091916 A1 | 6/2015 |
| WO | 2016065033 A1 | 4/2016 |

OTHER PUBLICATIONS

International Search Report and Written Opinion received for PCT Application No. PCT/IB2018/053985, dated Aug. 30, 2018, 9 pages.

* cited by examiner

BONE SCREW

FIELD

The present invention relates generally to bone screws and methods for using the same.

BACKGROUND

A variety of conditions can result in the need for manipulation or treatment of spinal conditions, and many spinal procedures require the use of one or more bone screws. In particular, bone screws, such as pedicle screws, can be used in the spine to correct deformities and treat trauma and/or degenerative pathologies. For example, bone screws can be used in instrumentation procedures to affix rods and plates to the spine, can be used to immobilize part of the spine to assist fusion by holding bony structures together, and can be used in a variety of other operations to treat spinal conditions. Bone screws can provide a means of anchoring or securing various elements to a spinal segment during these procedures.

It is important to quickly and accurately advance bone screws into bone during these operations to save time and expense by making the operations easier and faster for the surgeons. For example, many bone screws used in these procedures are pedicle screws, meaning they are a particular type of bone screw designed for implantation into a pedicle of a vertebra. Successfully advancing a bone screw into such a structure can be a significant challenge, adding difficulty and danger to an operation while possibly requiring additional equipment to ensure correct screw placement.

Accordingly, there remains a need for bone screws having an improved structure for successful placement in bone.

SUMMARY

Bone screws and methods for making and using a bone screw are provided herein. In one embodiment, a pedicle screw is provided that includes an elongate shank defining a central longitudinal axis. The elongate shank can have proximal and distal ends, and at least one thread formed on the elongate shank that extends between the proximal and distal ends. A distal-most end of the at least one thread can have a leading cutting edge extending transverse to the central longitudinal axis from an outer diameter of the screw toward the central longitudinal axis, and a leading surface can extend proximally from the leading cutting edge. The leading surface can extend at an acute angle relative to the central longitudinal axis of the elongate shank.

In some instances, the acute angle of the leading surface can be in a range of 5 to 15 degrees, and in certain embodiments can be approximately 10 degrees. In other embodiments, the at least one thread can be first and second threads that define an awl-shaped tip along a longitudinal cross-section. The bone screw can also include a trailing surface extending from the leading cutting edge, and the trailing surface and the leading surface can extend at an acute angle relative to one another. In other aspects, a radial outer edge of the distal-most end of the at least one thread can be arcuate.

In other embodiments, the pedicle screw can include a head on the proximal end of the elongate shank in which the head can have a drive feature for coupling with a driver. The elongate shank can have an inner lumen extending longitudinally therethrough. The elongate shank can also have first and second threads formed thereon. In some embodiments, the at least one thread can include a first thread having a constant thread pitch extending between the proximal and distal ends of the elongate shank, and a second thread that extends from the proximal end to a mid-portion of the elongate shank. In other embodiments, the elongate shank can have fenestrations formed therein.

In another embodiment, a bone screw is provided that has an elongate body including a longitudinal centerline extending between a first end and a second end thereof. A distal tip at the second end of the elongate body can have at least one cutting edge configured to cut bone, and the at least one cutting edge can have a positive rake angle. At least one thread can extend along the body from the at least one cutting edge towards the first end.

The bone screw can have numerous variations. For example, the distal tip can have an awl-shaped cross section along the longitudinal centerline. The bone screw can also have a head at the first end of the elongate body with a drive feature formed therein. A radial outer edge of the distal tip can be arcuate, and in some embodiments, the elongate body can have an inner lumen extending therethrough. The at least one thread can have a constant thread pitch. In other embodiments, the at least one thread can include a first thread extending between the first and second ends of the elongate body, and a second thread that can extend from the first end to a point between the first end and the second end of the elongate body, which can terminate before the second end and can have a constant thread pitch. The elongate body can also have fenestrations formed therethrough.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various bone screws and tip structures are provided that are configured to be implanted in bone. While the bone screws are described in connection with spinal operations and particularly placement in a pedicle of a vertebra, the screws can be used in connection with any type of bone, tissue (such as in a suture anchor or for lagging soft tissue to bone such as in a shoulder), or in other non-surgical applications. In an exemplary embodiment, a bone screw is provided with an elongate shank having a distal end or tip with one or more cutting edges that are configured to cut bone as the bone screw is threaded into bone. The cutting edge(s) can have a leading surface extending therefrom that has an acute rake angle that reduces a drag as the screw is rotated, while still effectively cutting the bone to facilitate insertion of the bone screw into bone.

FIGS. 1-5 illustrate one embodiment of a bone screw 100 with an elongate shank 102 having a proximal end 104, a distal end 106, and an inner lumen 108 extending entirely therethrough along a longitudinal axis L. The inner lumen 108 can be configured to receive a guidewire for facilitating placement of the bone screw in bone and/or bone cement to assist in anchoring the bone screw. The screw 100 can also include a head 112 having a drive feature 110 (shown in FIG. 8) configured to couple with a driver tool (not shown) for advancing the screw 100 into bone. The screw can have one or more threads formed therealong that terminate at a distal tip on the distal end 106 that is configured to cut bone.

Figure 8:
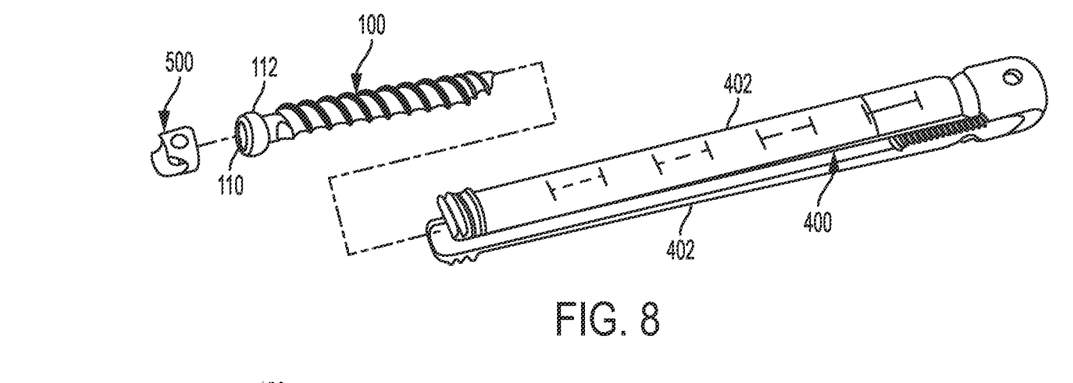
FIG. 8 is a perspective view of the bone screw of FIG. 1 shown with a receiver member and a compression cap to form a bone screw assembly.

The head 112 of the bone screw 100 can have various configurations, and various drive features can be formed in or on the head. The drive feature 110 shown in FIG. 8 is configured to receive a driver tool, such as a screw driver, a hexagonal driver, etc. Any complementary mating features can be used. In other embodiments, the head can be shaped to be received in a drive socket of a driver tool, or alternatively the bone screw can be headless.

The elongate shank 102 of the bone screw 100 can have various configurations. The elongate shank 102 shown in FIG. 1 has a cylindrical body with a constant diameter extending along a majority thereof, representing a diameter of the bone screw 100. The shank can be tapered, for example at the distal end, transitioning from a larger diameter to a smaller distal-most diameter. In other embodiments, the shank can taper along the entire length with a larger diameter at a proximal end of the shank tapering to a smaller diameter at a distal end thereof. Accordingly, tapering of the shank can be continuous along the length of the shank such that the diameter decreases at a constant rate along the length thereof, or tapering can be located just at a distal end thereof such that only a distal portion of the shank is tapered while a proximal portion has a constant diameter.

Figure 1:
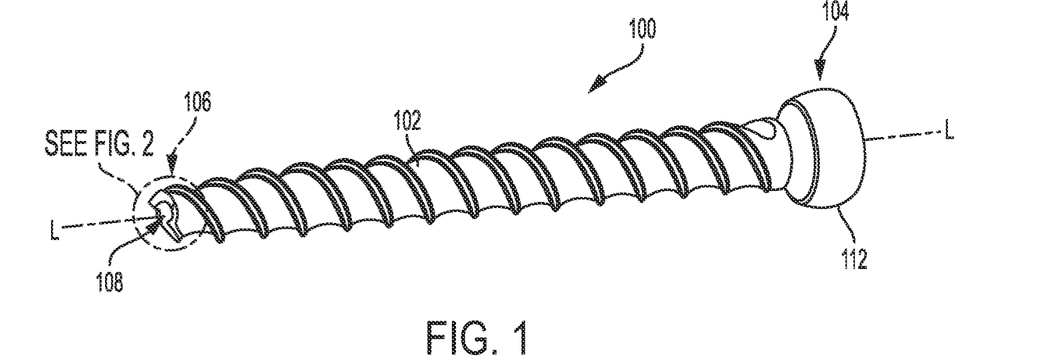
FIG. 1 is a perspective view of one embodiment of a bone screw.
Figure 2:
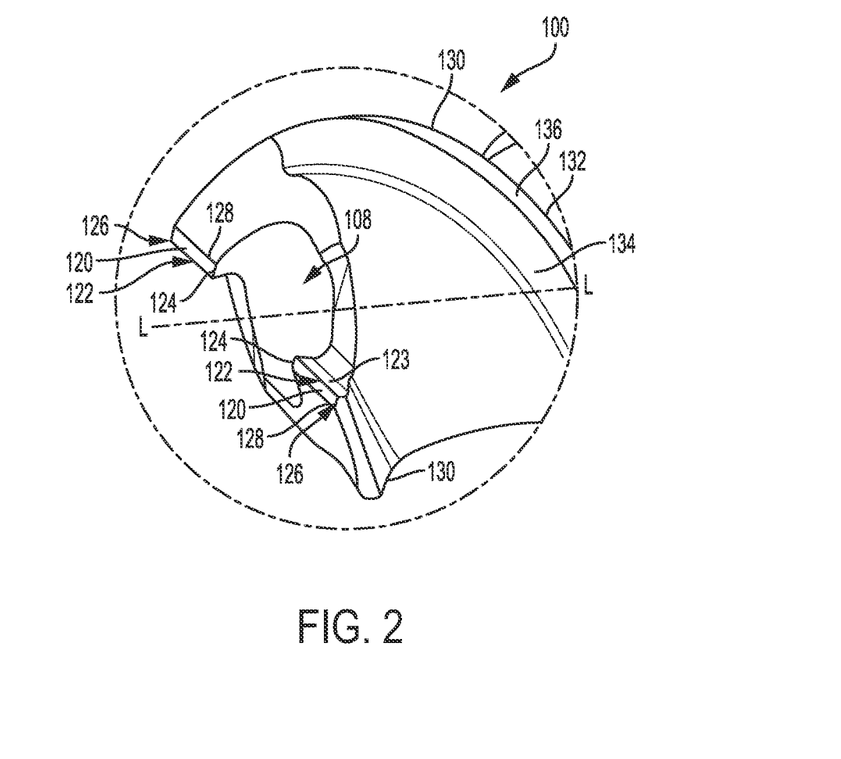
FIG. 2 is a perspective view of a distal tip of the bone screw of FIG. 1.

As indicated above, the elongate shank can include threads formed therealong. In the illustrated embodiment, the screw 100 has two threads 130 formed on an external surface thereof, but one or more threads can be used as discussed in further detail below. In the illustrated embodiment, the threads 130 start on opposite sides (e.g., 180 degrees apart) of the shank 102 so that they are opposed to each other and extend in a helix pattern along at least part of the elongate shank 102 between the proximal end 104 and the distal end 106. The threads 130 can each have a distal-most end that terminates in a cutting edge 122, as discussed in further detail below. The threads 130 can have an approximately constant thread pitch as well as a constant lead along the entire length of the shank 102.

Figure 6:
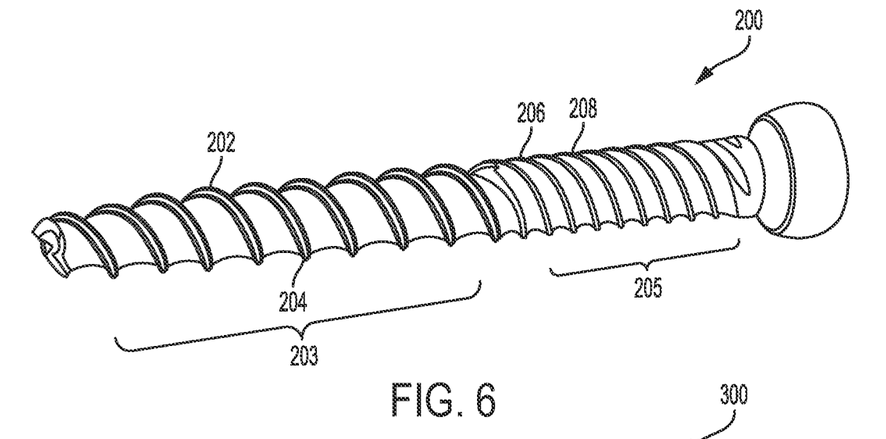
FIG. 6 is a perspective view of another embodiment of a bone screw.
Figure 7:
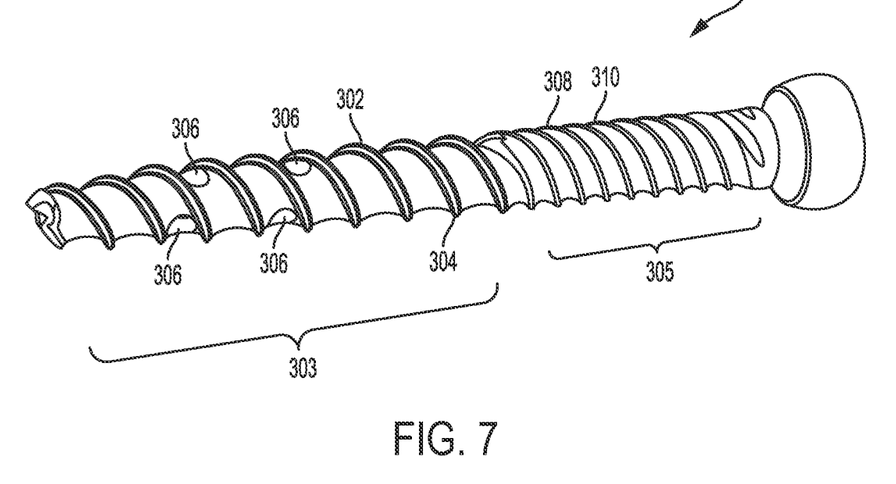
FIG. 7 is a perspective view of still another embodiment of a bone screw.

FIGS. 6 and 7 illustrate additional embodiments of bone screws 200, 300 that are similar to the bone screw 100. However, bone screws 200, 300 have first and second threads 202, 204, 302, 304 that have a constant thread pitch along a length thereof, and third and fourth threads 206, 208, 308, 310 that start at a proximal end and terminate at some point along the bone screws 200, 300 between proximal and distal ends thereof, for example approximately halfway at a mid-portion. While the thread lead for each thread can be constant, the addition of two more threads on a proximal portion of the bone screws 200, 300 can have the effect of increasing the thread pitch along the proximal portion 203, 303 of the bone screws 200, 300 as compared to a distal portion 205, 305. A person skilled in the art will appreciate that the thread pitch and the lead can vary as may be desired based on the intended use.

The threads discussed herein, including the number of threads, the pitch, the lead, major and minor diameters, and thread shape, can be selected to facilitate connection with bone. Additionally, the diameters of the threads can vary similar to the diameter of the elongate shank discussed above, wherein diameters of the thread(s) represent major diameters of the bone screws. As discussed above with the diameter of the elongate shank representing a minor diameter, the major and minor diameters of a bone screw can taper from one end to the other of a bone screw, such as from a proximal end to a distal end. The major and minor diameter taper can be the same or different. The start of the major and minor diameter taper can be at the same location along an elongate shank of a bone screw or can be different, resulting in constant crest width or varying crest width.

In the illustrated embodiment, each of the threads 130 has a proximal-facing surface 132, a distal-facing surface 134, and an outer-most surface 136 that can extend at an angle to the proximal and distal facing surfaces 132, 134. A thread profile of each of the threads 130 can be, for example, square or rectangular in shape. In other embodiments, the thread profile of the threads can be triangular, rounded, etc., and a height and a width of each of the threads can vary.

Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein in their entireties.

While threads are shown herein, other surface features can be used in other embodiments. For example, in some embodiments, bone screws can be configured to permit the screw to rotate in one direction but resist or prevent rotation in the opposite direction and/or can include cleats, spikes, friction-fit features, etc. formed thereon. Additionally, the bone screws can have fenestrations or openings formed therein, such as the fenestrations 306 formed on the screw 300 as illustrated in FIG. 7. The fenestrations 306 can be in the form of blind bores or thru-bores formed in a distal portion of the bone screw 300 and configured to allow for bone ingrowth or for secure attachment to bone. For example, bone screw 300 can be advanced through a pedicle structure and into a vertebral body, and cement can be injected into the vertebral body. Distal placement of the fenestrations 306 can be configured to reduce or prevent cement from flowing back into the pedicle structure, as well as being configured to direct cement flow to a distal end of the screw. For example, fenestrations can direct cement into cancellous bone surrounding a distal portion of a bone screw to create an optimal cement bolus or anchor to which the bone screw will be affixed. While the fenestrations 306 are positioned in the distal portion of the bone screw 300, fenestrations can be formed elsewhere in other embodiments. Exemplary systems for delivering bone cement to bone anchor assemblies and alternative bone anchor configurations for facilitating cement delivery are described in U.S. Patent Application Publication No. 2010/0114174, filed on Oct. 29, 2009, which is hereby incorporated by reference herein.

Referring back to FIGS. 1-5, the distal tip of the bone screw can have one or more cutting edges formed thereon and having a leading surface extending therefrom that is configured to facilitate cutting of bone during rotation of the bone screw into bone. As illustrated in FIGS. 2-5, each thread 130 terminates in a sharp leading or cutting edge 122 configured to cut bone as the screw is rotated into bone. Because the cutting edges 122 are at terminal ends of the threads 130 and the illustrated bone screw 100 is cannulated, the cutting edges 122 extend from an outer diameter of the bone screw toward the inner lumen 108 and are positioned on opposite sides of the inner lumen 108.

Each cutting edge 122 in the illustrated embodiment is defined by two surfaces extending from opposed sides thereof. The surfaces can be upper and lower surfaces of the threads 130, or one or both surfaces can be separately formed at an end of the thread 130. In the illustrated embodiment, the cutting edges 122 each have a leading surface 123 and a trailing surface 120 extending from opposed sides thereof, and thus defining the cutting edge 122. Surface 123 is referred to as a leading surface and surface 120 is referred to as a trailing surface due to the intended clockwise rotation of the bone screw for inserting the bone screw into bone.

Figure 3A:
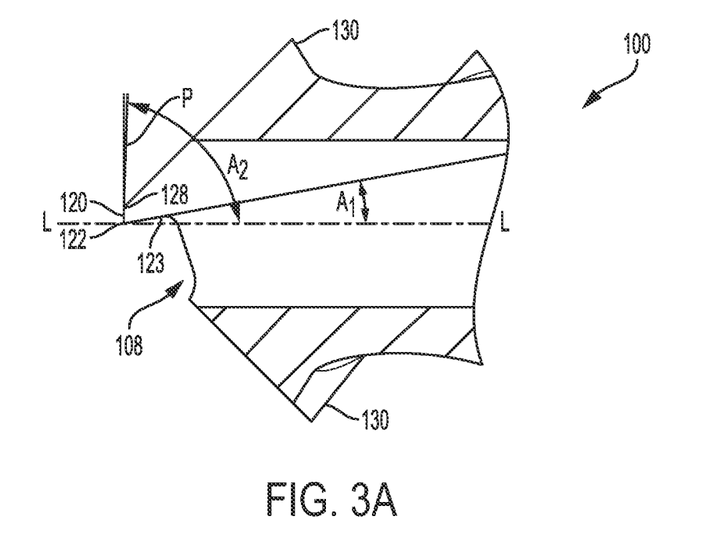
FIG. 3A is a cross-sectional side view of the distal tip of the bone screw of FIG. 1.
Figure 3B:
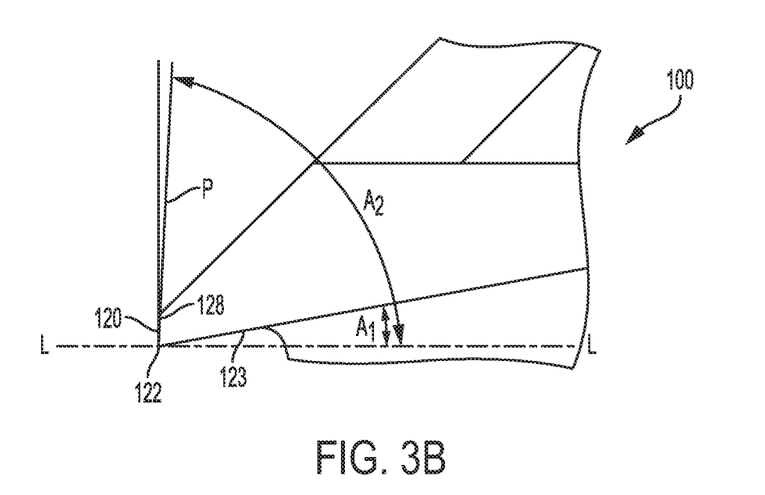
FIG. 3B is an enlarged cross-sectional side view of the distal tip of the bone screw of FIG. 3A.

Each leading surface 123 can extend proximally from the cutting edge 122 at an acute angle A1, i.e., less than 90 degrees, relative to the longitudinal axis L. The angle A1 provides a positive rake angle to the cutting edge 122 relative to bone. The angle A1 thus allows the cutting edge 122 to be configured to dig into and cut bone, with the leading surface 123 acting to force and/or drive the bone screw 100 into bone by redirecting applied torque while minimizing an axial force required for the bone screw 100 to advance into bone. In some embodiments, the angle A1 can be in a range of 5 to 15 degrees, and in certain embodiments can be approximately 10 degrees.

Figure 5:
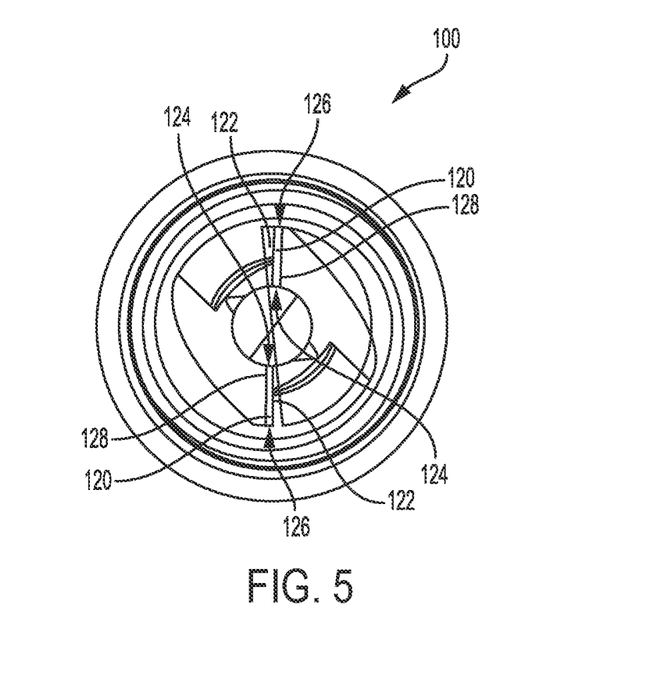
FIG. 5 is a distal-to-proximal end view of the bone screw of FIG. 1.

Each trailing surface 120 can extend from the cutting edge 122 in a direction opposite to the leading surface 123 and can be a substantially planar, distal-facing surface at a distal terminal end of the threads 130. In particular, each trailing surface 120 can be substantially flat and rectangular with four edges. As a result, each trailing surface 120 can have the leading or cutting edge 122 on one side thereof, a trailing edge 128 on an opposite side thereof, and two arcuate (or curved) edges. Inner-most edge 124 of the trailing surface 120 can be arcuate to match a curvature of the lumen 108, and outer-most edge 126 can likewise be arcuate to match a curvature of the thread 130 of the bone screw 100, as illustrated in FIG. 5.

Each trailing surface 120 can be inclined or angled proximally in a direction leading away from the cutting edge 122. As shown in FIG. 3B, each trailing surface 120 can extend along a plane P oriented at an acute angle A2 of less than 90 degrees relative to the longitudinal axis L, as illustrated in FIGS. 3A and 3B. In some embodiments, the angle A2 can be in a range of approximately 30 to 95 degrees, or more specifically 80 to 95 degrees, and in certain embodiments can be approximately 88 degrees. The trailing surface 120 can terminate in a trailing edge 128 which, as a result of the trailing surface 120 be inclined, can be located proximal of the cutting edge 122. Accordingly, because each trailing surface 120 is acutely angled, the trailing surfaces 120 can reduce or eliminate frictional drag when advancing the screw 100 into bone.

Figure 4:
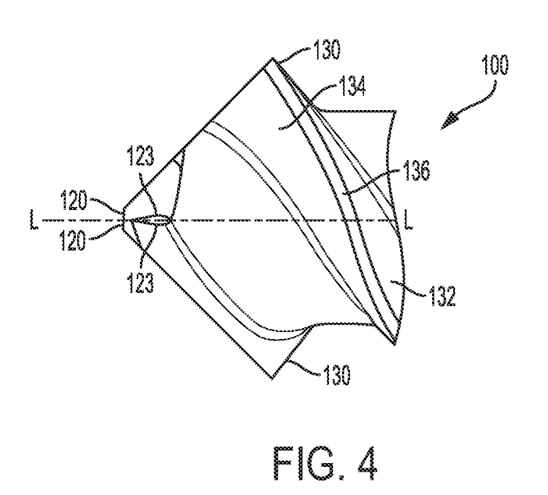
FIG. 4 is a side view of the distal tip of the bone screw of FIG. 1.

Because the trailing surfaces 120 are positioned approximately 180 degrees apart on opposite sides of the lumen 108, the distal tip of the screw 100, when viewed along a cross-section section extending through the axis L as shown in FIG. 4, can have the shape of an "awl" or "V" such that the bone screw is configured to allow effective docking in and piercing of bone, such as the cortical layer of bone of the pedicle. The "awl" or "V" shape can be present in both cannulated and non-cannulated bone screws. The distal tip of the bone screw 100, including the cutting edges 122 and the leading and trailing surfaces 123, 120, can thus be configured to maximize the efficiency of the bone screw 100 and to minimize the torque and downward force required to drive the bone screw 100 into bone.

In certain embodiments, the bone screw can be part of a bone anchor assembly. As illustrated in FIG. 8, the bone screw 100 can be used with a polyaxial receiver 400 and a compression cap 500. The receiver 400 can be in the form of a U-shaped body having screw extension tabs 402 extending proximally therefrom. The receiver 400 can have an inner cavity configured to seat the head 112 of the bone screw 100. The elongate shank 102 can extend through an opening in a distal end of the receiver 400. The compression cap 500 can be configured to be received in the receiver 400 and positioned proximally from the bone screw 100. A spinal rod (not shown) can be positioned between the screw extension tabs 402, and it can be seated in a proximal portion of the compression cap 500. The assembly can also include a set screw (not shown) configured to be received between the screw extension tabs 402, and it can apply a distal force to the spinal rod and the compression cap 500 to lock the rod within the receiver 400 and to lock the bone screw 100 in place relative to the receiver 400. The outer surfaces of each of the screw extension tabs 402 can include a feature, such as a recess, dimple, notch, projection, or the like, to facilitate connection of the receiver 400 to instruments. For example, the screw extension tabs 402 can include an arcuate groove at the respective free end of the tabs. Such grooves are described in more detail in U.S. Pat. No. 7,179,261, issued on Feb. 20, 2007, which is hereby incorporated by reference herein. Additionally, the bone screw 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor assembly can be a conventional (non-biased) polyaxial screw in which the bone screw pivots in the same amount in every direction.

The surgical instruments disclosed herein can be configured to operate in conjunction with bone anchor assemblies of the type described above or other types known in the art. As indicated above, it will be appreciated that the bone screw 100 of the bone anchor assembly can be a monoaxial screw, a polyaxial screw, a uniplanar screw, a bone hook, a favored-angle screw, a Modular screw, and/or any of a variety of other bone anchor types known in the art. Further information on favored-angle screws can be found in U.S. patent application Ser. No. 13/648,184, filed on Oct. 9, 2012, which is hereby incorporated by reference herein. The bone screw 100 and the bone anchor assembly can be used with various devices, such as the insertion device disclosed in U.S. patent application Ser. No. [ ], entitled "Spinal Screw Insertion Devices And Methods," filed on even date herewith, which is hereby incorporated by reference herein.

In use, the bone screw 100 can be inserted into a body of a patient, either as part of a screw assembly such as that illustrated in FIG. 8 or as part of another procedure. The distal end 106 of the bone screw 100 can be placed against bone, such as a vertebral pedicle. A driver tool (not shown) can engage the drive feature 110, and the driver tool can be rotated to rotate the bone screw 100, e.g., clockwise, relative to the bone. As the cutting edges 122 rotate, they can cut away bone and cause the screw 100 to advance forward into the bone. The threads 130 can engage edges of a bone hole, which can secure the bone screw 100 in the bone hole. The driver tool can continue to be rotated until the bone screw 100 is fully driven into the bone.

Figure 9:
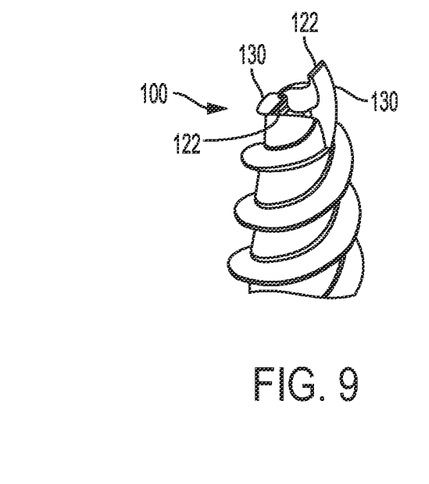
FIG. 9 is a perspective view of the distal tip of the bone screw of FIG. 1.
Figure 10:
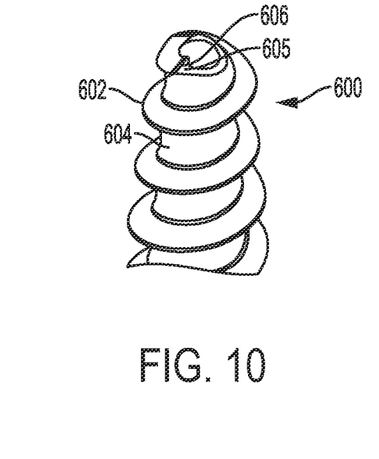
FIG. 10 is a perspective view of a distal tip of another embodiment of a bone screw.
Figure 11:
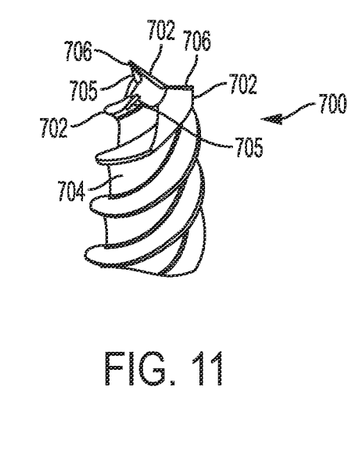
FIG. 11 is a perspective view of a distal tip of another embodiment of a bone screw.
Figure 12:
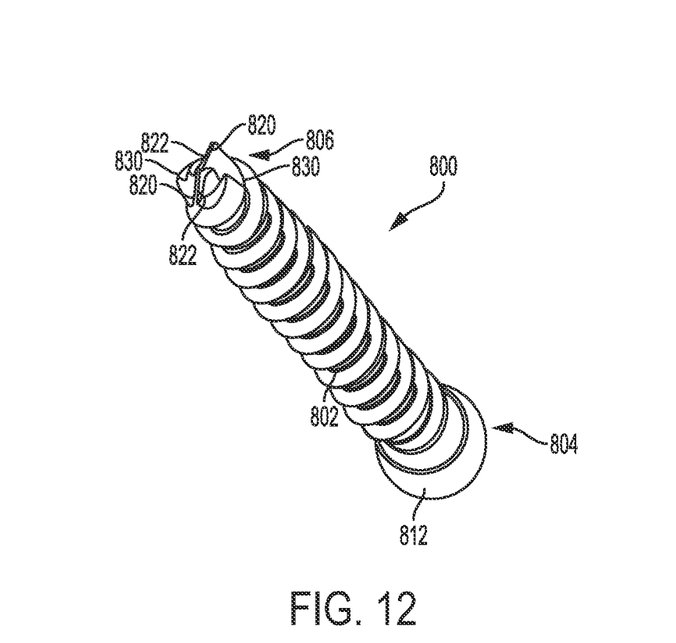
FIG. 12 is a perspective view of another embodiment of a bone screw.
Figure 13:
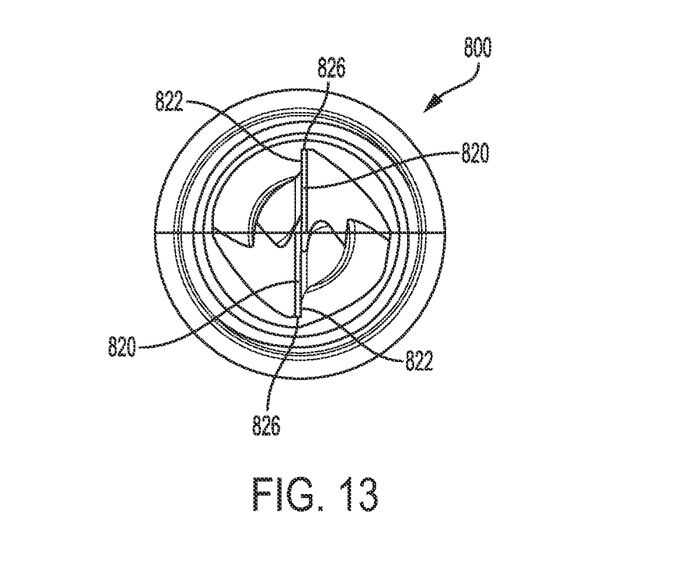
FIG. 13 is a distal-to-proximal end view of the bone screw of FIG. 12.
Figure 14:
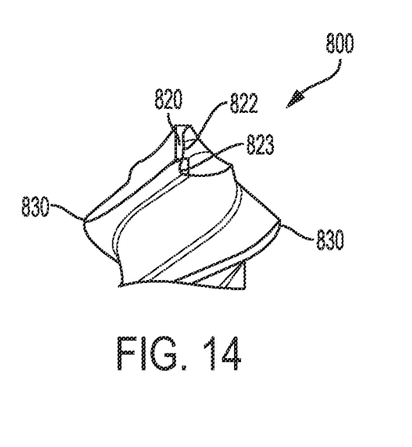
FIG. 14 is a perspective view of the distal tip of the bone screw of FIG. 12.
Figure 15:
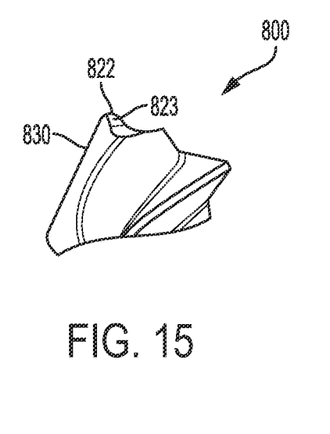
FIG. 15 is another perspective view of the distal tip of the bone screw of FIG. 12.
Figure 16:
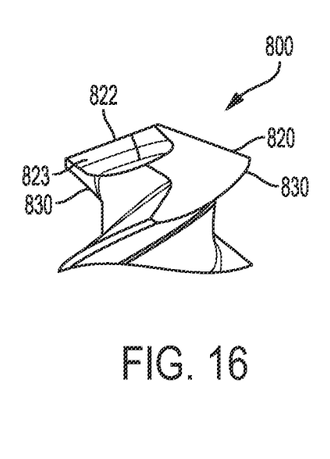
FIG. 16 is another perspective view of the distal tip of the bone screw of FIG. 12.

While the bone screw 100 has two threads 130 formed thereon, other embodiments can have one or more threads formed thereon and terminating in one or more cutting edges. For example, FIG. 9 illustrates bone screw 100 with two threads 130 and the cutting edges 122 formed thereon. FIG. 10 illustrates a bone screw 600 similar to bone screw 100 but with a single thread 602 extending along an elongate shank 604 with a leading surface 605 and terminating in a single cutting edge 606 at a positive rake angle similar to the cutting edges 122. FIG. 11 illustrates a bone screw 700 similar to bone screw 100 but with three threads 702 extending along an elongate shank 704 with leading surfaces 705 and terminating in three cutting edges 706 with positive rake angles similar to the cutting edges 122. Accordingly, any number of threads can be used, including one, two, three, four, five, etc.

Additionally, bone screws can have solid elongate shanks without any cannulation or lumens extending therethrough. FIGS. 12-16 illustrate an embodiment of a bone screw 800 similar to bone screw 100 but without any cannulation or any lumen therethrough. The bone screw 800 can have an elongate shank 802 having a proximal end 804 and a distal end 806. The screw 800 can also include a head 812 having a drive feature (not shown) configured to couple with a driver tool (not shown) for advancing the screw 800 into bone. The screw can have two threads 830 formed therealong that terminate in two cutting edges 822 with positive rake angles, similar to the cutting edges 122. Thus, leading surfaces 823 can extend proximally from the cutting edges 822. Two trailing surfaces 820 can also be formed at a distalmost end of the threads 830 that are each a substantially planar, distal-facing surfaces, and each trailing surface 820 can be substantially flat and rectangular with four edges. As with trailing surfaces 120, trailing surfaces 820 can each have an outer-most edge 826 that can be arcuate to match a curvature of the thread 830 of the bone screw 800. In other embodiments, the trailing surfaces do not have to be substantially planar and do not have to be substantially flat and rectangular with four edges. They can have a variety of forms, shapes, orientations, etc.

The screws disclosed herein can be formed from any of a variety of materials. In some embodiments, the screws can be formed from non-absorbable materials, such as polysulfone, or metals such as titanium and titanium alloys. In other embodiments, the screws can be formed from or can include a coating made of a biocompatible, bioabsorbable material that can reduce immunological problems associated with having a foreign substance within the body over a prolonged period of time. Exemplary materials from which the screws disclosed herein can be formed include bioabsorbable elastomers, copolymer combinations such as polylactic acid-polyglycolic acid (PLA-PGA), and bioabsorbable polymers such as aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. In some embodiments, the screws can be formed from polylactic acid, or a composite blend of tricalcium phosphate and polylactic acid. One or more coatings can be used on the bone screws, for example coatings to promote bone growth or improve bone adherence to the bone screw. The screws disclosed herein can be formed from a single, unitary material and structure or can be formed from one or more materials listed above.

The screws disclosed herein can be provided in any of a variety of sizes, depending on patient anatomy, procedure type, screw assembly size, and various other parameters which will be readily apparent to one having ordinary skill in the art. In some embodiments, the screws disclosed herein can be about 30 mm to 60 mm or about 80 mm to 100 mm in length, and about 4.5 mm, 5 mm, 6 mm, 7 mm, 7.5 mm, 10 mm, or 12 mm in diameter.

In some embodiments, a kit can be provided that includes one or more of the screws disclosed herein along with one or more screw assemblies, such as that illustrated in FIG. 8. For example, an exemplary kit can include a plurality of screws and/or screw assemblies of varying type and size, such that a surgeon can select the appropriate screw and/or screw assembly for a particular application.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components (e.g., spinal rods) with which the devices will be used, and the methods and procedures in which the devices will be used. The figures provided herein are not necessarily to scale. Although the devices and methods disclosed herein are generally directed to surgical techniques, they can also be used in applications outside of the surgical field. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A pedicle screw, the pedicle screw comprising:
an elongate shank defining a central longitudinal axis, the elongate shank having proximal and distal ends; and
at least one thread formed on the elongate shank and extending between the proximal and distal ends, a distal-most end of the at least one thread having a leading cutting edge extending along a line perpendicular to and passing through the central longitudinal axis from an outer diameter of the screw toward the central longitudinal axis, a leading surface extending proximally from the leading cutting edge, the leading surface extending at an acute angle relative to the central longitudinal axis of the elongate shank and having a curved portion, a trailing surface extending from the leading cutting edge such that the leading surface and the trailing surface are opposite one another across the leading cutting edge, the trailing surface being a substantially flat planar distal-most surface, the trailing surface and the leading surface extending at an acute angle relative to one another, the trailing surface terminating in a trailing edge disposed opposite to the leading cutting edge across the trailing surface, and a third surface extending proximally from the trailing edge.

2. The pedicle screw of claim 1, wherein the acute angle of the leading surface relative to the central longitudinal axis is in a range of 5 to 15 degrees.

3. The pedicle screw of claim 1, wherein the acute angle of the leading surface relative to the central longitudinal axis is approximately 10 degrees.

4. The pedicle screw of claim 1, wherein a radial outer edge of the distal-most end of the at least one thread is arcuate.

5. The pedicle screw of claim 1, wherein the at least one thread comprises first and second threads that define an awl-shaped tip along a longitudinal cross-section.

6. The pedicle screw of claim 1, further comprising a head on the proximal end of the elongate shank, the head including a drive feature for coupling with a driver.

7. The pedicle screw of claim 1, wherein the elongate shank has an inner lumen extending longitudinally therethrough.

8. The pedicle screw of claim 7, wherein the curved portion of the leading surface extends at least partially along the inner lumen of the elongate shank.

9. The pedicle screw of claim 1, wherein the at least one thread comprises first and second threads that are offset from one another by 180 degrees.

10. The pedicle screw of claim 1, wherein the leading cutting edge extends substantially parallel to the trailing edge.

11. The pedicle screw of claim 1, wherein the trailing edge is proximal of the leading cutting edge along the central longitudinal axis of the elongate shank.

12. The pedicle screw of claim 1, wherein the trailing surface is defined by the cutting edge, a radial outer edge, the trailing edge, and a radial inward edge, the cutting edge and the trailing edge are each longer than the radial outer edge and the radial inward edge.

13. The pedicle screw of claim 1, wherein the trailing surface extends along a plane oriented at an acute angle of less than 90 degrees relative to the longitudinal axis.

14. A bone screw, the bone screw comprising:
an elongate body having a longitudinal centerline extending between a first and a second end thereof;
a distal tip at the second end of the elongate body having at least one cutting edge configured to cut bone, the at least one cutting edge having a positive rake angle, the at least one cutting edge extending along a line perpendicular to and passing through the longitudinal centerline of the elongate body, the at least one cutting edge being defined between a leading surface and a trailing surface, the leading surface extending proximally from the cutting edge and having a curved portion, the trailing surface being a substantially flat planar distal-most surface on the distal tip; and
at least one thread extending along the body from the at least one cutting edge towards the first end.

15. The bone screw of claim 14, wherein the distal tip has an awl-shaped cross-section along the longitudinal centerline.

16. The bone screw of claim 14, further comprising a head at the first end of the elongate body with a drive feature formed therein.

17. The bone screw of claim 14, wherein a radial outer edge of the distal tip is arcuate.

18. The bone screw of claim 14, wherein the elongate body has an inner lumen extending therethrough.

19. The bone screw of claim 14, wherein the at least one thread has a constant thread pitch.

20. The bone screw of claim 14, wherein the at least one cutting edge comprises first and second cutting edges, the leading surface comprises first and second leading surfaces, and the trailing surface comprises first and second trailing surfaces; and
wherein the first cutting edge, the first leading surface, and the first trailing surface are positioned on an opposite side of the longitudinal centerline of the elongate body from the second cutting edge, the second leading surface, and the second trailing surface.

* * * * *

UNITED STATES PATENT AND TRADEMARK OFFICE
CERTIFICATE OF CORRECTION

PATENT NO. : 11,376,050 B2
APPLICATION NO. : 15/633969
DATED : July 5, 2022
INVENTOR(S) : John DiVincenzo et al.

Page 1 of 1

It is certified that error appears in the above-identified patent and that said Letters Patent is hereby corrected as shown below:

In the Specification

At Column 7, Lines 11-12, delete "patent application Ser. No. 13/648,184, filed on Oct. 9, 2012" and insert --Patent Application Publication No. 2013/0096618, filed on October 9, 2012-- in place thereof At Column 7, Lines 17-18, delete "patent application Ser. No. [____], entitled "Spinal Screw Insertion Devices And Methods" and insert --Patent No. 10,433,883, issued on October 8, 2019-- in place thereof Signed and Sealed this
Third Day of February, 2026

John A. Squires
*Director of the United States Patent and Trademark Office*